(12) United States Patent
Carter et al.

(10) Patent No.: US 7,130,696 B2
(45) Date of Patent: Oct. 31, 2006

(54) PERCUTANEOUS ELECTRODE ARRAY

(75) Inventors: John Carter, Belle Harbor, NY (US); Bradford Siff, Westport, CT (US)

(73) Assignee: Biowave Corporation, Norwalk, CT (US)

(*) Notice: Subject to any disclaimer, the term of this patent is extended or adjusted under 35 U.S.C. 154(b) by 33 days.

(21) Appl. No.: 10/956,105

(22) Filed: Oct. 4, 2004

(65) Prior Publication Data

US 2005/0043775 A1 Feb. 24, 2005

Related U.S. Application Data

(60) Division of application No. 10/459,695, filed on Jun. 10, 2003, now Pat. No. 7,013,179, which is a continuation-in-part of application No. 09/756,999, filed on Jan. 8, 2001, now Pat. No. 6,584,358.

(60) Provisional application No. 60/175,003, filed on Jan. 7, 2000, provisional application No. 60/183,258, filed on Feb. 17, 2000.

(51) Int. Cl.
 *A61N 1/34* (2006.01)
(52) U.S. Cl. ............... 607/69; 607/46; 607/67; 607/70; 607/74; 29/825; 29/857
(58) Field of Classification Search .......... 607/46, 607/67, 69, 70, 72, 74, 76; 29/825, 857
See application file for complete search history.

(56) References Cited

U.S. PATENT DOCUMENTS

| 2,622,601 A | 12/1952 | Nemec |
|---|---|---|
| 3,096,768 A | 7/1963 | Griffith, Jr. |
| 3,170,993 A | 2/1965 | Puharich et al. |
| 3,393,279 A | 7/1968 | Flanagan |
| 3,563,246 A | 2/1971 | Puharich |
| 3,586,791 A | 6/1971 | Puharich |
| 3,727,616 A | 4/1973 | Lenzkes |
| 3,774,620 A | 11/1973 | Hansjurgens |
| 3,794,022 A | 2/1974 | Nawracaj et al. |
| 3,958,577 A | 5/1976 | Rodler |
| 4,023,574 A | 5/1977 | Nemec |
| 4,071,033 A | 1/1978 | Nawracaj et al. |
| 4,153,061 A | 5/1979 | Nemec |
| 4,177,819 A | 12/1979 | Kofsky et al. |
| 4,220,830 A | 9/1980 | Schafer |
| 4,231,372 A | 11/1980 | Newton |
| 4,280,504 A | 7/1981 | Rodler |

(Continued)

FOREIGN PATENT DOCUMENTS

JP 5092045 4/1996

OTHER PUBLICATIONS

Electro-Acuscope 70C Specifications—Biomedical Design Instruments "Electro-Acuscope 70" http://www.designmed.com/70c.htm, (4 pages).

(Continued)

*Primary Examiner*—Shawntina Fuqua
(74) *Attorney, Agent, or Firm*—Dickstein, Shapiro, LLP.

(57) ABSTRACT

A method of producing percutaneous electrode array is disclosed for applying therapeutic electrical energy to a treatment site in the body of a patient. The array comprises a plurality of electrode microstructures which are inserted into the epidermis, thereby overcoming the inherent electrical impedance of the outer skin layers and obviating the need to prepare the skin surface prior to an electro-therapy treatment. The array preferably includes an adhesion layer to help keep the electrode microstructures inserted into the epidermis during the duration of the therapeutic treatment, and temperature and condition monitoring devices to ensure proper treatment and enhance patient safety.

6 Claims, 11 Drawing Sheets

U.S. PATENT DOCUMENTS

| | | |
|---|---|---|
| 4,401,121 A | 8/1983 | Rodler |
| 4,580,570 A | 4/1986 | Sarrell |
| 4,595,010 A | 6/1986 | Radke |
| 4,699,679 A | 10/1987 | Cartmell et al. |
| 4,711,243 A | 12/1987 | Schafer |
| 4,848,347 A | 7/1989 | Hall |
| 4,909,255 A | 3/1990 | Farin |
| 4,960,124 A | 10/1990 | Masaki |
| 4,977,895 A | 12/1990 | Tannenbaum |
| 4,989,605 A | 2/1991 | Rossen |
| 5,107,835 A | 4/1992 | Thomas |
| 5,123,413 A | 6/1992 | Hasegawa et al. |
| 5,161,530 A | 11/1992 | Gamble |
| 5,250,023 A | 10/1993 | Lee et al. |
| 5,269,304 A | 12/1993 | Matthews |
| 5,324,317 A | 6/1994 | Reiss |
| 5,458,625 A | 10/1995 | Kendall |
| 5,512,057 A | 4/1996 | Reiss et al. |
| 5,573,552 A | 11/1996 | Hansjurgens |
| 5,593,432 A | 1/1997 | Crowther et al. |
| 5,643,330 A | 7/1997 | Holsheimer et al. |
| 5,713,922 A | 2/1998 | King |
| 5,776,173 A | 7/1998 | Madsen, Jr. et al. |
| 5,782,873 A | 7/1998 | Collins |
| 5,948,007 A | 9/1999 | Starkebaum et al. |
| 5,950,635 A | 9/1999 | Garcia-Rill et al. |
| 5,983,141 A | 11/1999 | Sluijter et al. |
| 6,011,994 A | 1/2000 | Kronberg |
| 6,032,060 A | 2/2000 | Carim et al. |
| 6,058,577 A | 5/2000 | Ida et al. |
| 6,064,911 A | 5/2000 | Wingrove |
| 6,161,048 A | 12/2000 | Sluijter et al. |
| 6,169,813 B1 | 1/2001 | Richardson et al. |
| 6,210,574 B1 | 4/2001 | Sammons et al. |
| 6,230,051 B1 | 5/2001 | Cormier et al. |
| 6,256,533 B1 | 7/2001 | Yuzhakov et al. |
| 6,379,324 B1 | 4/2002 | Gartstein et al. |
| 6,451,002 B1 | 9/2002 | Dev et al. |
| 6,503,231 B1 | 1/2003 | Prausnitz et al. |
| 6,525,030 B1 | 2/2003 | Eriksson |
| 6,544,258 B1 | 4/2003 | Fleenor et al. |

OTHER PUBLICATIONS

Electro-Acuscope 80L Electro-Myopulse 75L; http://www.acuscope.com/italy/itl.htm, (8 pages).

Griss et al., "Characterization of Micromachined Spiked Biopotential Electrodes," 49 IEEE Transactions on Biomedical Engineering 597-604 (Jun. 2002).

Henry et al., "Microfabricated Microneedles: A Novel Approach to Transdermal Drug Delivery," 87 Journal of Parmaceutical Sciences 922-25 (Aug. 1998).

PERCUTANEOUS ELECTRODE ARRAY

CROSS REFERENCE TO RELATED APPLICATIONS

This is a divisional application of U.S. patent application Ser. No. 10/459,695, filed Jun. 10, 2003 now U.S. Pat. No. 7,013,179 which is a continuation-in-part of U.S. patent application Ser. No. 09/756,999, filed Jan. 8, 2001, now U.S. Pat. No. 6,584,358, which claims priority to U.S. provisional application No. 60/175,003, filed on Jan. 7, 2000 and also to U.S. provisional application No. 60/183,258, filed on Feb. 17, 2000, each of which is hereby incorporated by reference for each of its teachings and embodiments.

FIELD OF THE INVENTION

This invention relates to an electro-therapy method and apparatus and more particularly to a method and apparatus for applying a therapeutic electrical signal for relieving pain arising from temporary or chronic conditions or during or after surgery.

BACKGROUND OF THE INVENTION

Electro-therapy is the application of electrical energy to the body of a human patient to provide a therapeutic effect. The therapeutic effects produced by electro-therapy include the blockage of pain, residual pain relief possibly due to the release of endorphins or other opiate-like analogs, relief from headache pain, increase of blood flow, increases in the range of motion, cartilage regrowth or regeneration, accelerated bone growth, electronic epidural for childbirth and other beneficial effects that result from the introduction of a low frequency electric field into tissue beneath the skin. Electro-therapy as defined by this application does not include electro-osmosis, electroporation, or iontophoresis, or any other process in which electrical energy such as an electrical field or electric currents are used to promote the transdermal transportation of chemicals or fluids into or out of the body. Nor does it include electrosurgery where radiofrequency electrical energy is used to cut or cauterize tissue.

Electro-therapy typically employs a non-invasive technique to introduce the electrical energy into the patient's body. Disposable electrode pads are placed on the epidermal surface of a patient and coupled to an electric generator. The generator supplies two or more oscillating or complex morphology electric currents to a patient, with respective selected electrode pads separated from one another on the patient's body with a pain site located between the electrode pads with the majority of the electric field positioned perpendicular to each skin surface on which the pads reside. The electric currents have frequencies of at least about 1 KHz and differing by as little as 1 Hz up to about 250 Hz from each other. A non-linear action of nerve fiber membranes and/or other electrochemically-active structures or fluids causes a mixing of the two independent frequency signals in a volume of tissue surrounding and beneath the pads along an axis between them to produce a therapeutic effect. The mixing yields a distribution of synthesized sum and difference frequencies among which is a therapeutic low frequency equivalent to a beat frequency of the signals.

In order to penetrate the tissue beneath the skin and provide a therapeutic effect, electrical signals applied to the body must overcome the electrical impedance of the skin. Electrical impedance is a property of the skin that limits the amount of current that can pass through the skin. The top layer of the skin, the stratum corneum, is made up of dead skin cells and contributes to the skin's high electrical impedance. Dry, intact skin can have an impedance which exceeds a hundred thousand ohms. Even carefully prepared skin, i.e., where the hair has been shaved or otherwise removed, where debridement of devitalized or contaminated tissue has been performed, and where the skin's surface has been moisturized, can still have an impedance of over one thousand ohms. A potentially large voltage would be necessary to overcome the skin impedance and drive a therapeutically useful amount of electrical current through body tissues. The relatively large amount of energy required limits the amount of time that a portable generator device powered by batteries can be used.

Additionally, electrical currents may travel across or just beneath the surface of the skin, further reducing the amount of useful current provided to body tissues. This leakage current arises from the various layers of skin, and can limit the range of frequencies that can be applied to body structures. The skin layers contribute electrical capacitance and resistive properties which act as a barrier to current flow, thus requiring a larger power source to compensate for the leakage current, further limiting battery lifetime.

Biomedical studies conducted in other unrelated fields have determined ways to reduce skin impedance. For example, one study involved the use of a silicon micro-needle array to evaluate large-molecule transportation properties of the array/skin interface (See Henry, S. et al., "Microfabricated Microneedles: A Novel Approach to Transdermal Drug Delivery," 87 J. Pharm. Sci. 922–925 (1998)). A micro-needle array is an array of small injection needles having a limited length so that a sufficient quantity of drugs can be injected though the needles into the skin, without the accompanying pain perceived by the patient as with a standard injection needle. Volunteers described the sensation of a micro-needle array insertion as being similar to affixing a piece of tape to the skin. This study showed that the micro-needle array caused a 50-fold drop in skin resistance.

In another study, an array of silver or silver with silver chloride coated spikes were used as electrodes for electro-encephalography (EEG), i.e., the measurement of electrical activity of the brain. (See Griss, P. et al., "Characterization of Micromachined Spiked Biopotential Electrodes," 49 IEEE Trans. Biomed. Eng. 597–604 (2002)). The array was applied to the forehead of the patient to monitor EEG activity. The array was used to overcome skin resistance in order to detect the weak EEG electrical signals produced by the brain.

In addition, patents have been granted for needle arrays used in conjunction with iontophoresis and electroporation. In iontophoresis, and electric field is used to accelerate ionized molecules for addition to or removal from the body. For example, Gartstein et al. disclose in their U.S. Pat. No. 6,379,324 issued on Apr. 30, 2002 a molded or cast plastic micro-needle array in combination with an anode and cathode electrodes. Ionized drugs are accelerated into the body due to the applied electric potential. Additionally, the array uses an electric field to remove fluid from the body for analysis by a biological electrochemical sensor.

In electroporation, short pulses of high electric fields are applied to the cells causing the cell wall to transiently become porous. The applied electric field is adjusted to ensure that permanent damage to the cell wall does not result. Dev et al. disclose in their U.S. Pat. No. 6,451,002 issued on Sep. 17, 2002 a method for the treatment of tumors using an array of needles. High amplitude electrical signals are applied to the needles that cause electroporation of the tissue cells between the needles. Drugs used to treat the tumor are injected through the needles contemporaneously with the electroporation, thereby increasing their introduction into the tissue cells.

Electrosurgery is the use of electrical radio frequency energy to cut tissue and coagulate bleeding during surgery. In such a procedure, the electrical energy is delivered to the patient through a probe. The probe permits the physician to direct the electrical energy to the areas of the patient's body that she wishes to cut. In order to complete the electrical circuit, a return electrode is applied to the patient. The return electrode employs a large surface area contacting the patient to reduce the current density and prevent burning of the patient's skin at the return electrode. For example, Fleenor et al. disclose in their U.S. Pat. No. 6,544,258 issued Apr. 8, 2003 a self-regulating and self-limiting electrosurgical return electrode pad. A patient lies down on top of the pad during an electrosurgical procedure. The pad has a large surface area designed to prevent high current densities and temperature rise, thereby preventing patient trauma.

Electrode pads designed for use with medical test procedures such as electrocardiograms (ECGs) typically employ an electrical conductor, such as a lead wire, electrically connected to an electrolyte disposed within the electrode pad. For example, Cartmell et al. discloses in their U.S. Pat. No. 4,699,679 issued on Oct. 13, 1987 a disposable medical electrode pad that includes two foam sheets with electrically conductive adhesive layers on their lower surfaces. The pad further includes an electrolyte gel matrix between the foam sheets. These pads are designed for monitoring electrical signals produced by the patient, but are sometimes used to apply stimulation signals to a patent, such as in electrotherapy.

It is known in the art that applying electrical energy to the skin can reduce the impedance of the skin For example, Carim et al. discloses in their U.S. Pat. No. 6,032,060 issued on Feb. 29, 2000 directing electrical energy through a medical electrode placed on the skin of the patient in order to electrically condition the skin. The reduction in skin impedance increases the ability to monitor bioelectric signals and can reduce the amount of energy necessary for electroporation or transdermal iontophoresis.

Each of the above references provide and devices are designed for sensing electrical signals generated by the body, for delivering pharmaceuticals to the body, or for performing electrical surgery on the body. These devices disclosed by the references have physical characteristics and electrical properties which make them suitable for their intended uses; however, they are not designed for electrotherapy.

SUMMARY OF THE INVENTION

A percutaneous electrode array is disclosed for applying therapeutic electrical energy to a treatment site in the body of a patient. The array comprises a plurality of electrode microstructures which are inserted into the epidermis, thereby overcoming the inherent electrical impedance of the outer skin layers and obviating the need to prepare the skin surface prior to an electro-therapy treatment. The array preferably includes an adhesion layer to help keep the electrode microstructures inserted into the epidermis during the duration of the therapeutic treatment, and temperature and condition monitoring devices to ensure proper treatment and enhance patient safety.

In one aspect, the present invention is directed to a percutaneous electrode array for delivering therapeutic electrical energy to a patient, comprising: a substrate having a top side and a bottom side; and a plurality of electrodes each having a proximal end, a distal end, an axis from the proximal end to the distal end, and a length along the axis, wherein each electrode is attached to the top side of the substrate; wherein the electrodes have a total surface area of more than 0.2 square centimeters.

In another aspect of the present invention, the electrodes are substantially a cylinder and have a diameter of 20 to 250 micrometers.

In another aspect of the present invention, the electrodes are substantially a rectangular parallelepiped having a pair of narrow sides, a pair of wide sides, a top side and a bottom side, and wherein the wide sides have a width of 20 to 250 micrometers.

In another aspect of the present invention, the wide sides have a width of about 200 micrometers.

In another aspect of the present invention, the length of the electrodes is between 120 and 500 micrometers.

In another aspect of the present invention, the length of the electrodes is between 150 and 200 micrometers.

In another aspect of the present invention, the distal end of each electrode is one or more of thinned and pointed to facilitate placement into skin.

In another aspect of the present invention, the axis of the electrodes is perpendicular to the substrate.

In another aspect of the present invention, the axis of the electrodes is angled between perpendicular and parallel to the substrate.

In another aspect of the present invention, the substrate comprises a shape-memory metal alloy.

In another aspect of the present invention, the electrodes comprise one or more of doped semiconductor material, silicon-metal compound, stainless steel, conductive polymer, carbon allotrope, and a conductive metal either in bulk or deposited material.

In another aspect of the present invention, a temperature element is bonded to the substrate.

In another aspect of the present invention, the temperature element is one of a thermistor, a diode, a semiconductor junction, and a thermocouple.

In another aspect of the present invention, the array further comprises an adhesion layer.

In another aspect of the present invention, the array further comprises a plurality of voids that pass through the top side of the substrate to the bottom side; and an adhesion layer comprising a bottom side, a top side, and a plurality of protrusions extending above the top side; wherein the top side of the adhesion layer is attached to the bottom side of the substrate, and the protrusions pass through the voids to a first height above the top side of the substrate.

In another aspect of the present invention, the electrodes extend above the first height of the adhesion layer between 150 and 200 micrometers.

In another aspect of the present invention, the electrodes have a total surface area above the first height of the adhesion layer of at least 0.2 square centimeters.

In another aspect of the present invention, the adhesion layer comprises an electrically conductive hydrogel.

In another aspect of the present invention, the adhesion layer comprises a removable medical adhesive.

In another aspect of the present invention, the adhesion layer changes color as a function of ambient conditions.

In another aspect of the present invention, the array further comprises a capacitive plate disposed on the bottom side of the adhesion layer and an electrically insulating layer disposed on the capacitive plate opposite the adhesion layer.

In another aspect of the present invention, the array further comprises a temperature element embedded in the adhesion layer.

In another aspect, the present invention is directed to a percutaneous electrode array for delivering therapeutic electrical energy to a patient, comprising: a substrate having a top side and a bottom side; and a plurality of electrodes each having a proximal end, a distal end, an axis from the proximal end to the distal end, and a length along the axis, wherein each electrode is attached to the top side of the substrate, the substrate has a surface area of greater than 14.1 square millimeters and the electrodes have a total surface area of less than 0.2 square centimeters.

In another aspect, the present invention is directed to an electrode for delivering therapeutic electrical energy to a patient, comprising: a substrate having a first side and a second side; an adhesion layer comprising a bottom side and a top side attached to the first side of the substrate; a capacitive plate disposed on the bottom side of the adhesion layer; and an electrically insulating layer disposed on the capacitive plate opposite the adhesion layer.

In another aspect, the present invention is directed to an electrode for delivering therapeutic electrical energy to a patient, comprising: a substrate having a first side and a second side; and a temperature element bonded to the substrate.

In another aspect, the present invention is directed to a method of producing a percutaneous electrode array comprising: micromachining a master mold of a percutaneous electrode array having a substrate and a plurality of electrodes from silicon using semiconductor lithographic processing; creating a replica mold by electroplating thin film silver followed by nickel onto the master mold; heating, softening, and rolling a polymeric film; forcing the film into the replica mold using pressure to form an array structure; and cooling the array structure and removing the structure from the replica mold.

In another aspect of the present invention, the method further comprises thermally processing array material to form a carbonized structure; and depositing an adhesive layer on the structure.

In another aspect of the present invention, the polymeric film comprises polymethyl methacrylate.

In another aspect of the present invention, the method further comprises spraying conductive inks onto the structure and heating the structure to form a conductive coating.

In another aspect of the present invention, the method further comprises spraying, dipping or spin coating an indium tin oxide precursor onto the array structure; and heating the structure to form a conductive film coating.

In another aspect of the present invention, the method further comprises forming a conductive film comprising indium tin oxide by evaporation or sputtering processes onto the array structure.

In another aspect, the present invention is directed to a method of introducing therapeutic electrical energy to body tissues in a treatment site beneath the epidermis of a patient, comprising: providing an electro-therapy apparatus comprising: a signal generator configured to produce first and second signals; and a first and second percutaneous electrode array; positioning the first array on a first portion of the patient's body and positioning the second array on a second portion of the patient's body such that the first and second arrays are positioned on the tissue of the patient, and the treatment site is located between the first and second arrays; forming a therapeutic signal from said first and second signals; and introducing the therapeutic signal through the first and second arrays.

DETAILED DESCRIPTION OF THE INVENTION

The preferred embodiment disclosed provides for the application of therapeutic electrical signals to the body through a percutaneous electrode array. The array efficiently delivers therapeutic electrical energy into the body provided by an electro-therapy generator device. An electro-therapy generator device suitable for the production of such energy is described in U.S. patent application Ser. No. 09/756,999, entitled "Electro-Therapy Method and Apparatus," filed on Jan. 8, 2001, which is hereby incorporated by reference in its entirety for each of its teachings and embodiments.

Figure 1:
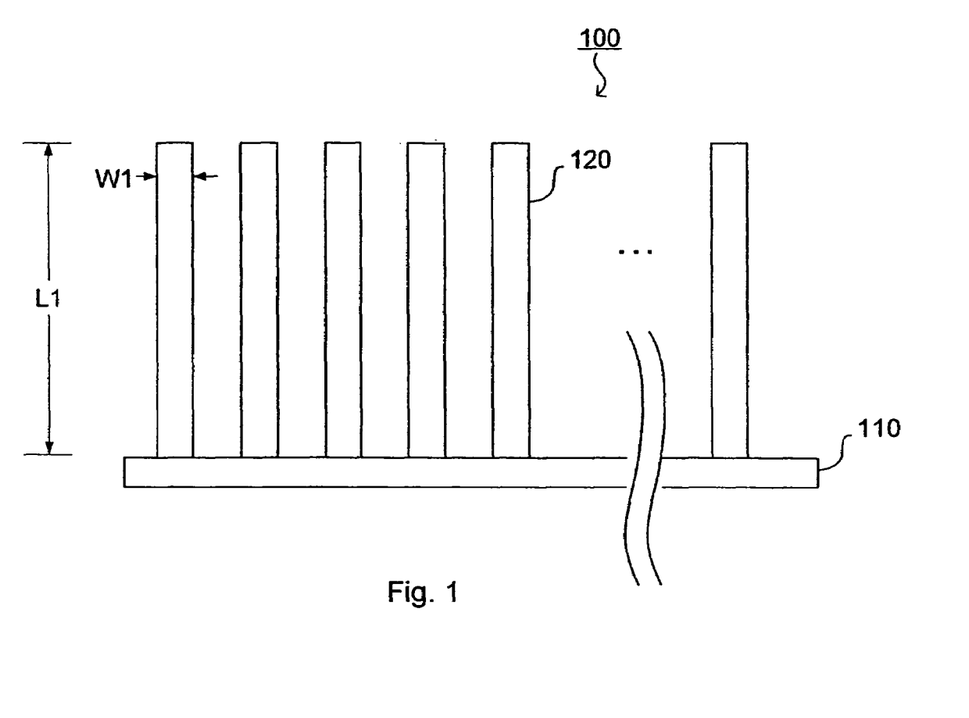
FIG. 1 is a side view of a percutaneous electrode array.

The configuration of a percutaneous electrode array is shown in FIG. 1. As shown in FIG. 1, the array comprises a substrate 110 and a plurality of electrodes 120. Electrodes 120 are attached to a top side of substrate 110. An electrical connection to the array is made on the bottom side of substrate 110 and preferably the entire bottom surface of the array is protected with an insulating material, for example a woven plastic or fabric cover.

Preferably, each electrode 120 comprises a rectangular parallelepiped attached at a proximal end to the substrate. Alternatively, each electrode 120 preferably comprises a cylinder or cone. The distal end of either electrode embodiment preferably further comprises one or more of a rounded triangular and pointed tip. The width or diameter W1 of each electrode is preferably between 20 to 250 micrometers.

The total surface area of the electrodes in the array equals the area of each electrode times the number of electrodes in contact with the skin. This area must be large enough to carry the electrical current introduced into the body by the electro-therapy generator device, while limiting the current density through the attached skin area. The surface area of each electrode comprises the area of the distal tip of the electrode plus the surface area along the effective length of the electrode, L1, i.e. the length that is inserted into the skin. Preferably, the total electrode surface area is greater than 0.2 square centimeters.

In an alternate preferred embodiment, the total electrode surface area is less than 0.2 square centimeters, but the substrate has a surface area greater than 14.1 square millimeters. The current conducting area of the substrate in combination with the area of the electrodes limits the current density to the skin.

The effective contact area of the electrodes is equal to the total surface area of the electrodes times a 56% reduction factor that accounts for the electrode element surface area which comes in contact with the body's ionic environment (70% of the electrode's length), and the number of electrodes that are in contact with the skin (80% of the total number of electrodes in the array). The Food and Drug Administration (FDA) currently limits the current density for electro-therapy devices to less than 10 milliamps per square centimeter of contact area. One with skill in the art will recognize that several different configurations can be employed in order to achieve the necessary effective contact area needed to reduce the current density below the FDA limit. One way to increase the area is to increase the length L1 of each electrode 120 in the percutaneous electrode array, i.e., the length in contact with the ionic environment of the body, in order to maximize the area for electrical conduction. The maximum length is determined by observing the structure of the skin in the human body.

Figure 2:
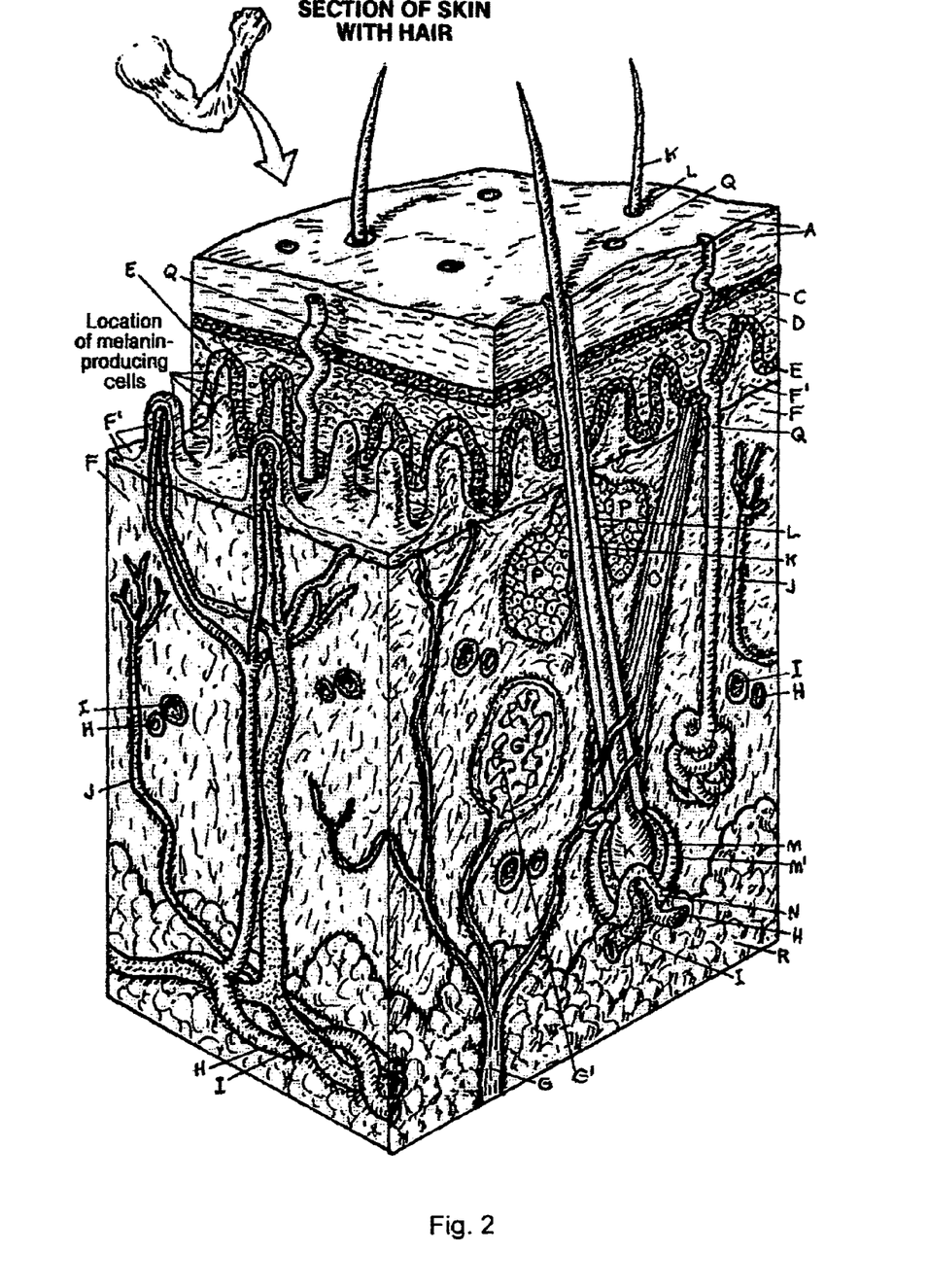
FIG. 2 is a cross-sectional view of human skin.

FIG. 2 illustrates a typical cross section of skin. The top layer of skin disclosed in FIG. 2, the stratum corneum, is comprised mostly of dead skin cells. Other layers beneath the stratum corneum include the stratum lucidly, stratum granulosum, stratum spinosum and the stratum basale. These five layers are collectively known as the epidermis. The epidermis covers the germinating skin layers, known as the dermis, which also contains nerves, arteries, veins, or lymphatic vessels. Depending on the location of the skin and its condition, the thickness of the epidermis is approximately 120 to 500 um. The effective length of electrodes 120 is preferably between 120 and 500 um, and more preferably between 150 and 200 um so that the tip of electrode 120 penetrates into the epidermis, but does not reach any nerves, arteries, veins, or lymphatic vessels. The effective length of the electrodes is preferably adapted to the location where the array is attached and to the condition of the skin within that region of body. The electrode length is tailored to match these variables, enabling the electrode array to successfully transit to a point just past the epidermis. This region is mostly devoid of pain receptors, making the insertion of the percutaneous electrode array virtually painless. The elastic properties of the skin helps seal holes left behind by electrodes 120 after the array has been removed. Furthermore, the small diameter of each electrode 120, about the diameter of a typical human hair, will limit the amount of fluid that could flow through the hole created by the electrode.

The major axes of electrodes 120 are preferably perpendicular to substrate 110, but may be angled between perpendicular and parallel to the substrate. Altering the mechanical properties of substrate 110 and/or electrodes 120 may enhance adhesion of the array to the skin. The electrical contact integrity can be improved or maintained by increasing the tension along the plane of substrate 110 between electrodes 120 and the skin surrounding the region of penetration. For example, substrate 110 may act as a spring. In this example, array 100 would be flexed prior to insertion. When array 100 is released, the tension stored in substrate 110 would force electrodes 120 against the skin.

In an alternative preferred embodiment, array 100 comprises a shape-memory metal, e.g., Nitinol. The transition temperature of the alloy is preferably correlated with skin temperature by formulation and processing of the alloy. An array 100 made from such materials would preferably expand or contract along a designated axis along the surface area of substrate 110. The expansion or contraction would force electrodes 120 laterally against the skin.

Electrodes 120 are preferably composed of material having good electrical conductive properties, such as doped silicon, silicon-metal compounds, nickel/iron alloy, stainless steel, conductive inks, an allotrope of carbon such as glassy carbon derived from high carbon content polymer pyrolysis, conductive polymers, polymer/graphite or polymer/metal composite blends, and other biocompatible metals. The materials also have sufficient shear strength to prevent the fracture of electrodes in the skin. In the preferred embodiment, the array comprises type 316 stainless steel.

As demonstrated above, the dimensions of the percutaneous electrode array are extremely small. The development of such small structures are known in the art as micro electrical mechanical systems, or MEMS. MEMS is a multidisciplinary field encompassing microelectronic fabrication, polymerization techniques, physical chemistry, life sciences and mechanical engineering. This cross-field environment has led to the development of micro and nano-sized structures such as micro-sensors, micro-motors and blood chemistry systems-on-a-chip. The manufacture of some percutaneous electrode array embodiments may draw on knowledge from this field, as discussed below.

In an alternative preferred embodiment, glassy carbon electrodes can be made from any high carbon content polymer, such as pitch and polyacrylonitrile. The material is formed into the micro-eletromechanical structures described above using the LIGA process. LIGA is a micromachining technology in which X-ray radiation is used in the production of high-aspect ratio, precision microstructures. LIGA parts are typically 2D extruded metal shapes, but 3D structures can be created using this process. In the process, a master mold is created from silicon using semiconductor lithographic processing. This mold is used to make replica molds by electroplating thin film silver followed by nickel. The replica mold has a thickness of 0.3 mm or greater depending on the mechanical loads borne by it. Next, polymeric material is heated and softened and rolled into a film. The film is placed against the replica. Pressure is applied to force the polymeric material into the mold. After a short time period, the temperature is reduced and the pressure removed.

Once the piece is formed, it is fired at 400 C to drive off volatile chemicals and to thermoset the plastic. This is followed by an 800 C bake in inert atmosphere to form carbonized material. The piece is further baked at about 1100 C to increase conductivity by forming a graphitic phase. Due to the small size of the electrodes, the relatively low strain properties of the material do not present a breakage problem, even after many insertion cycles.

In an alternative preferred embodiment, conductive inks are sprayed onto the electrode array formed from a polymer such as polymethyl methacrylate, or PMMA. Moderate heating to about 120 C increases both the conductivity and adhesion of the conductive film.

In another alternative preferred embodiment, indium tin oxide is applied to a PMMA electrode array. A glycol-metal precursor of indium tin oxide is sprayed or spin-coated onto the array and then heated to about 400C to form a conductive film coating. Indium tin oxide coatings exhibit superb conductivity properties.

In another alternative preferred embodiment, a polymer blend is used to form the array. In such an array, a large amount of either metal powder or graphite powder or graphite-nanofiber is added to a plastic precursor to render the final material moderately conductive. Aggregation of high concentrations of the conductive material can lead to poor uniformity in the surface conductivity of the final composite device. Thermal processing of the composite, where some of the volatile components of the mixture are driven off, may help to reduce this deleterious effect.

In another alternative preferred embodiment, pure metal is electrodeposited on a master mold defining the electrode structure. Preferably, the metal has a conductivity between 100 and 10000 S/cm.

Figure 3:
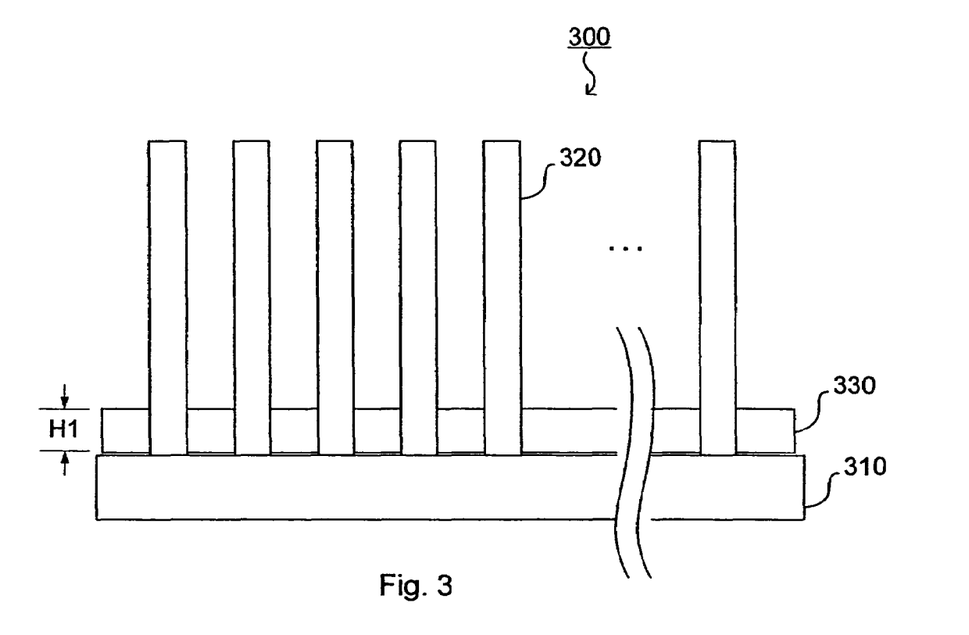
FIG. 3 is a side view of a percutaneous electrode array comprising an adhesion layer.

In an alternate embodiment, an adhesion layer is added to the array to increase the conductivity of the array and adhere the array to the skin. FIG. 3 illustrates a percutaneous electrode arrays that includes an adhesion layer. Array 300 comprises a substrate 310, a plurality of electrodes 320, and an adhesion layer 330. In a preferred method of manufacture, adhesion layer 330 is added to percutaneous electrode array 300 by depositing material to form the layer on the surface of substrate 310 between electrodes 320, or by piercing a sheet of layer material with array 300. Other methods may be evident to one with skill in the art.

Figure 3A:
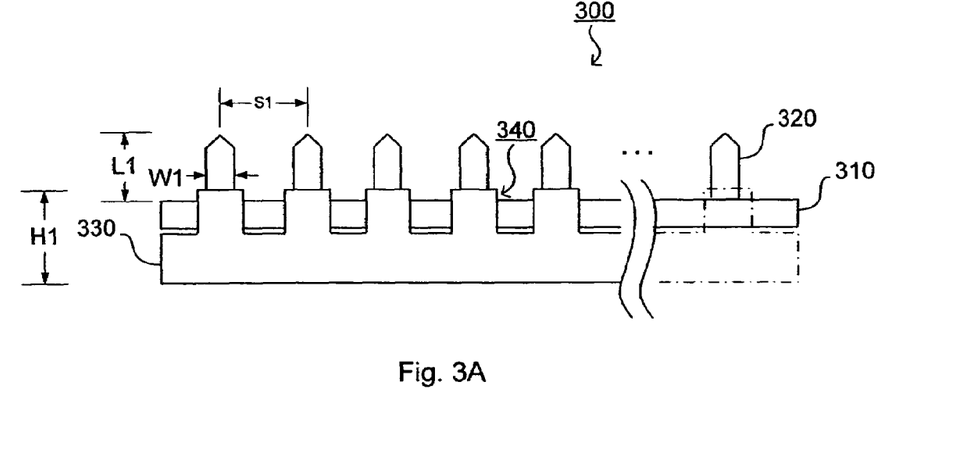
FIG. 3A is an exemplary embodiment of a percutaneous electrode array comprising a substrate with voids and an adhesion layer.
Figure 3B:
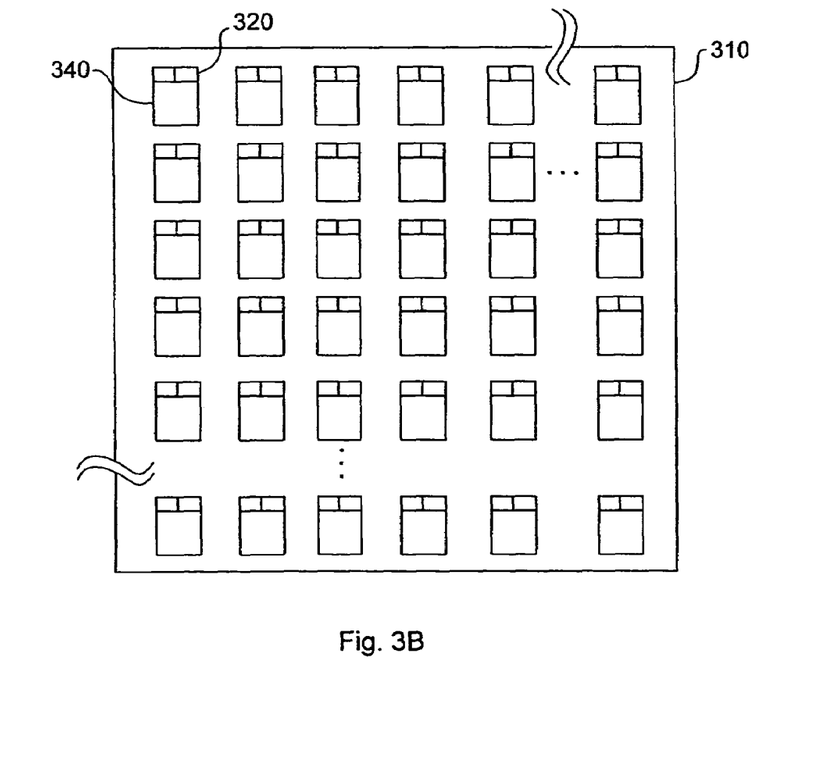
FIG. 3B is a top view of a percutaneous electrode array for use with an adhesion layer.
Figure 3C:
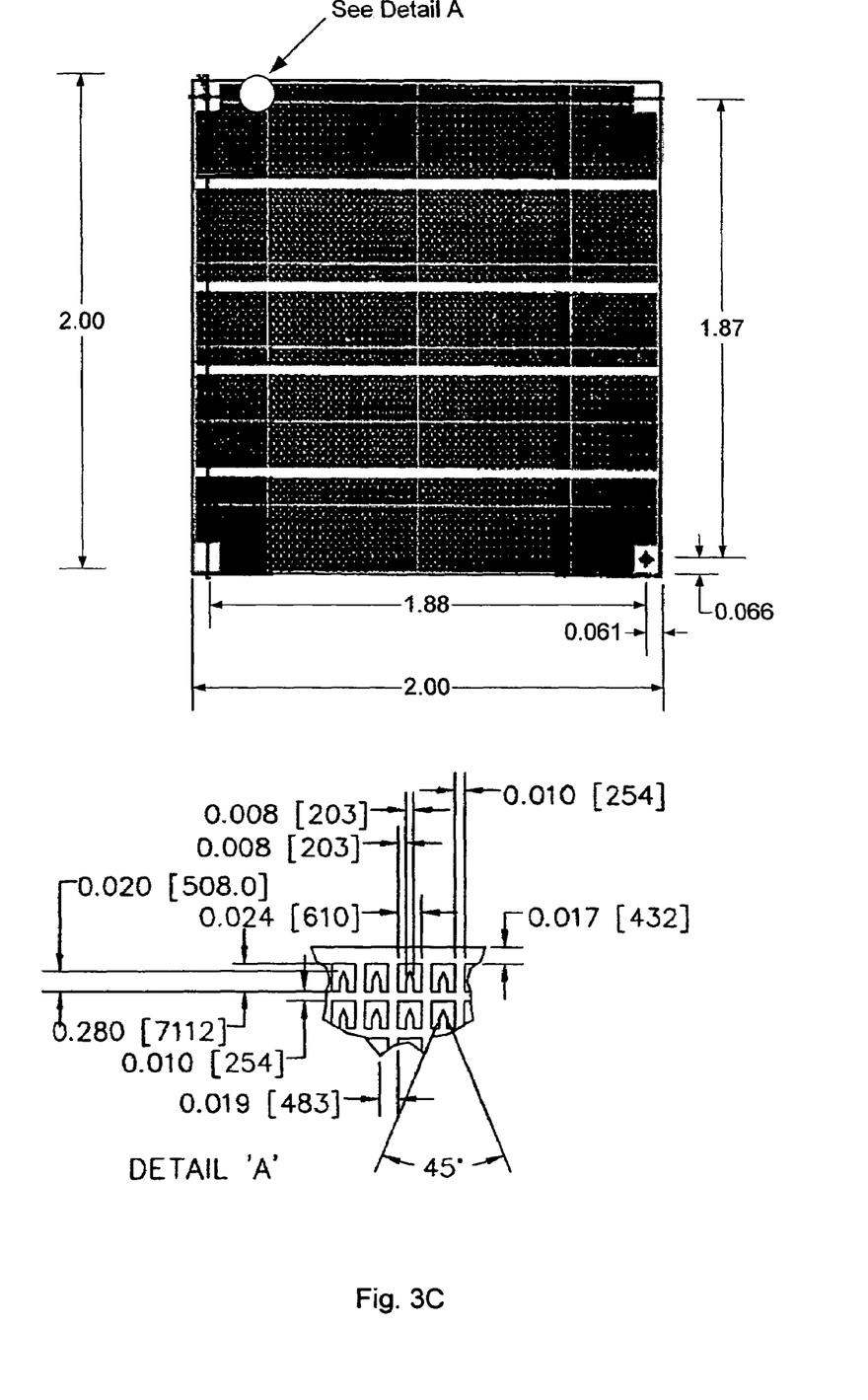
FIG. 3C is a mechanical drawing illustrating an exemplary embodiment of a percutaneous electrode array substrate and electrodes.

FIGS. 3A–3C illustrate a preferred embodiment of a percutaneous electrode array that includes an adhesion layer. More specifically, array 300 illustrated in FIG. 3A comprises a substrate 310, a plurality of electrodes 320, an adhesion layer 330, and a plurality of voids 340 in substrate 310. Adhesion layer 330 is mounted to a rear side of substrate 310 and protrudes through voids 340 in substrate 310. Adhesion layer 330 secures the electrode to the patient, and preferably aids in the conduction of the electrical signal into the body. Substrate 310 provides support for adhesion layer 330.

FIG. 3B depicts a top view of array 300 before application of adhesion layer 330. Electrodes 320 and voids 340 are arranged in a grid pattern. Preferably, array 300 is manufactured from a sheet of stainless steel stamped and/or etched to produce voids 340 and electrodes 320 within the area of voids 340. Electrodes 320 are bended upward so that the major axis is in the desired direction, preferably normal to the surface of substrate 310.

FIG. 3C is a mechanical drawing depicting an exemplary embodiment of percutaneous electrode array 300. The array comprises 3600 electrodes arranged in a regular grid pattern of 60 by 60. The width W1 of each electrode is approximately 200 um. A distance S1 of about 860 um separates the electrodes. These dimensions result in a 5 cm by 5 cm array of electrodes. Detail A shows the electrodes within the void area before they are bent upwards.

Suitable materials for use in layer 330 are a hydrogel or sol-gel construct containing an electrolyte. The minimum height of the hydrogel layer, H1, is limited by the estimated evaporation time and the mechanical modulus of the gel. In a preferred embodiment, the array comprises a 635 um thick conductive gel, e.g. Uni-Patch type RG63B. As the hydrogel is exposed to the air, the water in the gel will evaporate, drying out the array and reducing the adhesive and conductive properties of the gel. The use of such an array would require a higher applied voltage. If the array is flexed or the skin/array mechanical interface is otherwise altered, an instantaneous drop in interfacial impedance can occur, giving rise to an unpleasant feeling in the patient and concentrating the current at points of good contact, raising the possibility of a thermal burn. Adhesion layer 330 is preferably adapted to provide an indication that the array is no longer suitable for use.

In a preferred embodiment, the hydrogel contains materials well known in the art that, when exposed to air after the packaging material containing the electrode is opened, causes the hydrogel to slowly change color as a function of the evaporation rate. For example, the hydrogel may have a normally clear appearance, but would turn into a dark color after exposure to the atmosphere. Alternatively, the, normal appearance of the hydrogel may be colored, and after exposure the hydrogel turns clear. Such color changes indicate that the array needs to be replaced or that the integrity of the packaging is compromised and that the array is no longer sterile. In an alternate preferred embodiment, after the hydrogel has come into direct contact with human skin, a chemical reaction would occur which changes the color of the hydrogel without leaving any residue on the skin.

Figure 4:
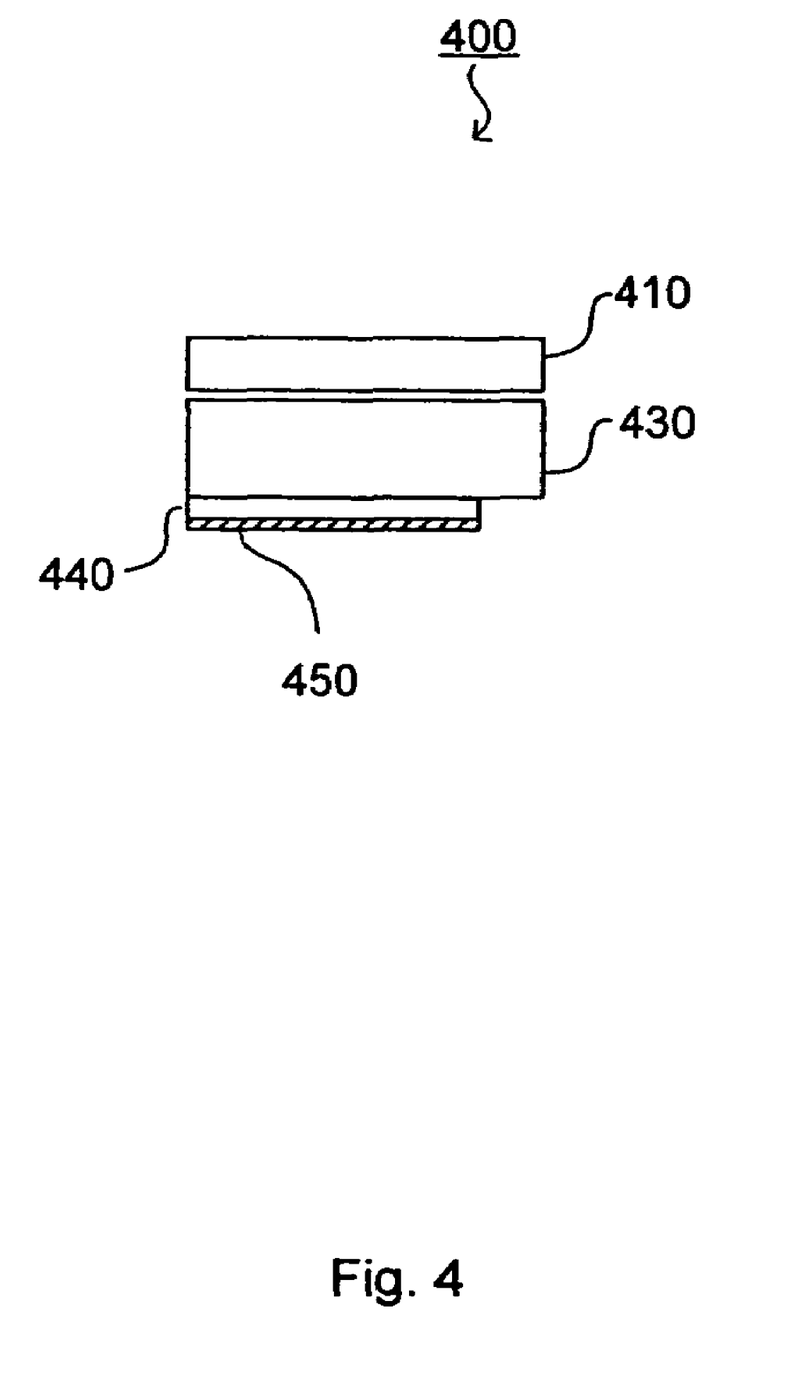
FIG. 4 is a side view of an electrode substrate and an adhesion layer having an integrated capacitive element.

In an alternative preferred embodiment, an adhesion layer of an electrode is monitored to determine if the array has dried out or if the temperature is increasing by measuring the electrical capacitance of the adhesion layer. FIG. 4 discloses the components of this embodiment. As shown in FIG. 4, the electrode comprises a substrate 410, an adhesion layer 430 and a capacitive plate 440 covered by an insulating layer 450. Capacitive plate 440 comprises a small section of conductive material on the bottom side of adhesion layer 430, thus forming an electrical capacitor comprising a dielectric (adhesion layer 430) between two conductive plates (substrate 410 and plate 440). The capacitance of the array capacitor is a function of both temperature and moisture content. An electrical lead is connected to plate 440 for connection in a monitoring circuit. Insulating layer 450 is coated over plate 440 to prevent plate 440 from electrically contacting the patient or others.

Figure 5:
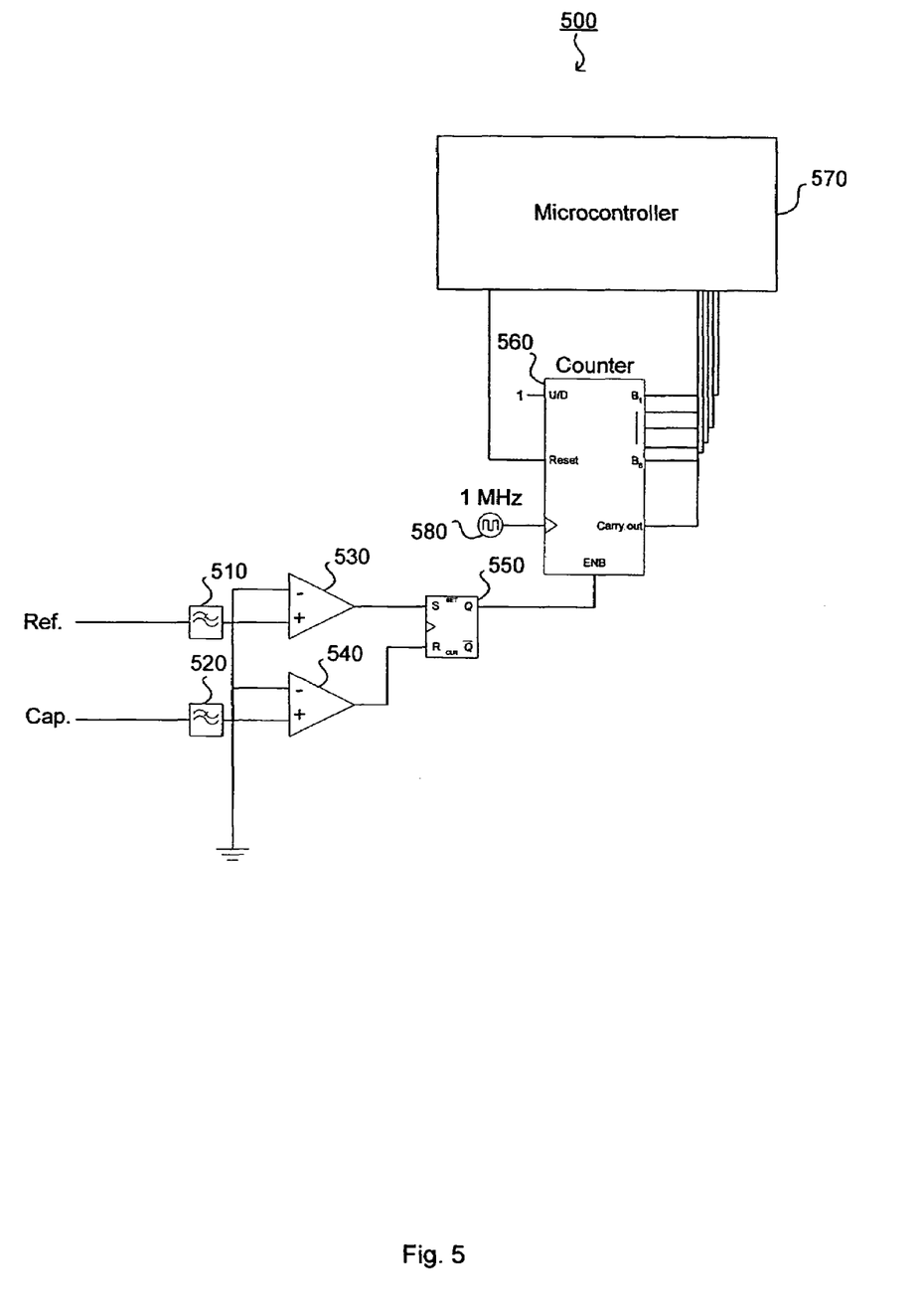
FIG. 5 is an exemplary circuit for measuring the capacitance of the capacitive element.

Circuits that measure capacitance are well known in the art. An exemplary circuit for measuring the array capacitance is illustrated in FIG. 5. Measuring system 500 comprises a pair of identical low-pass filters 510, 520, a pair of low-offset comparators 530, 540, a flip-flop 550, a binary counter 560, a microcontroller 570 and a high frequency clock 580. A stable sinusoidal signal, a component of the signal generated by the electro-therapy generator device described in more detail in U.S. patent application Ser. No. 09/756,999, entitled "Electro-Therapy Method and Apparatus," filed on Jan. 8, 2001, is used to determine the capacitance of adhesion layer 430.

Substrate 410 and capacitive plate 440 are connected to a monitoring circuit comprising low-pass filters 510, 520. Filters 510, 520 preferably comprise 8-pole switched capacitor filters that pass a stable sinusoidal signal. Comparators 530, 540, detect the zero crossings of the stable sinusoidal output applied to the reference, a fixed precision resistor, and the array capacitor. Reference comparator 530 sets flip-flop 550, which starts counter 560, and capacitance comparator 540 resets flip-flop 550, which stops counter 560. High frequency clock 580 provides a clocking signal to counter 560 which increments the counter once it is started. Counter 560 counts until the capacitance signal performs its zero crossing. Microcontroller 570 reads the count and then resets counter 560. Thus, counter 560 measures the time difference between the zero crossings of the reference signal and the current through the capacitor. Microcontroller 570 determines the phase shift between the signals from the count, which is indicative of the capacitance of the array capacitor. This measurement is independent of the amplitude of the two signals. Microcontroller 570 comprises embedded software that uses this information to determine if the change in capacitance represents a fault state. If such a determination is made, it can shut the system down and inform the user of the error condition. The software requires that a specific profile of the change in capacitance be maintained during system operation.

Figure 6:
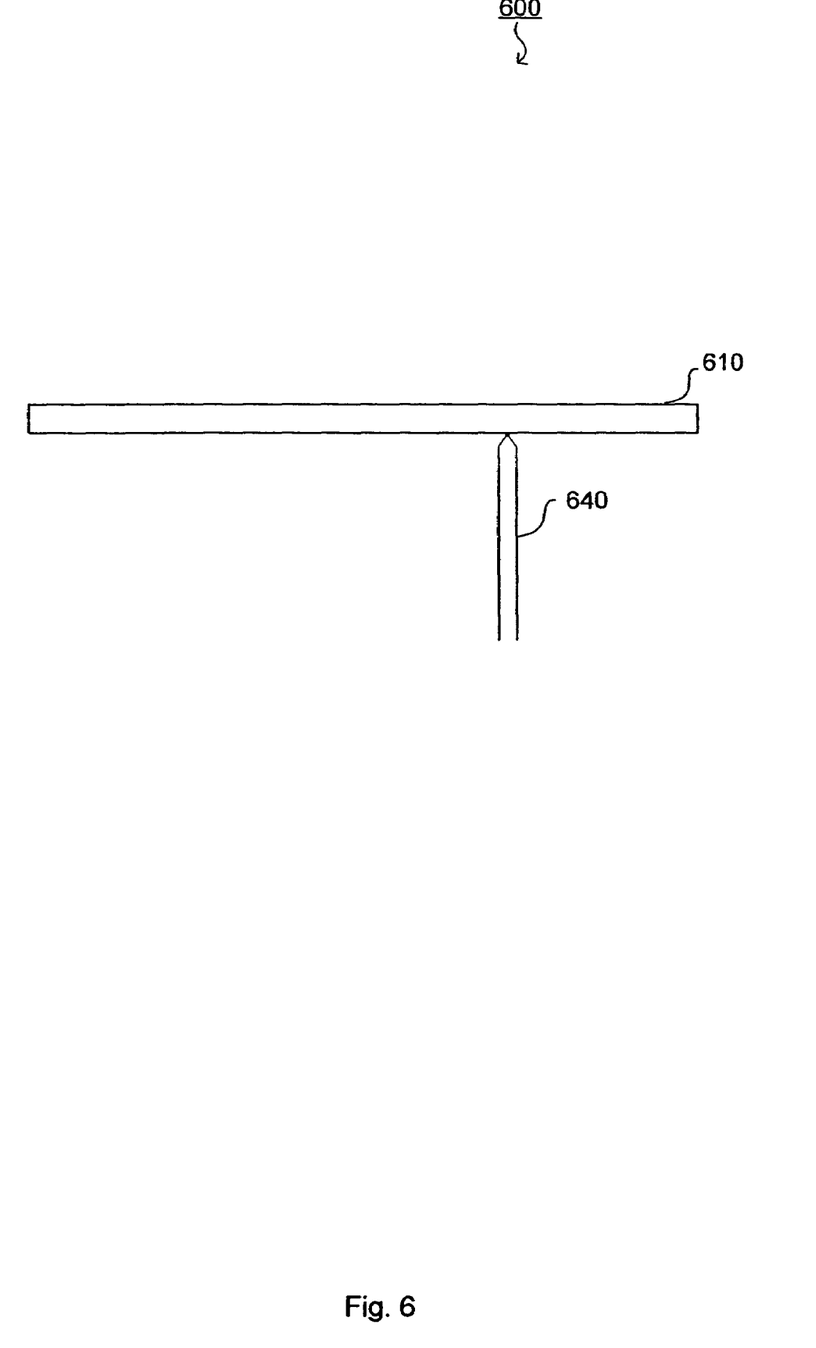
FIG. 6 is a side view of an electrode comprising an integrated thermal-sensing element.

FIG. 6 discloses a preferred embodiment of an electrode comprising a substrate 610 and a temperature-sensing element 640 bonded to substrate 610. The element comprises one of a thermistor, a diode, or other semiconductor junction, and a thermocouple. In a preferred embodiment, temperature element 640 is a small device, typically no more than 0.5 mm in thickness. Temperature element 640 accurately measures the temperature of substrate 610.

In an alternative preferred embodiment, an electrode comprising an adhesion layer has temperature-sensing element 640 embedded in the adhesion layer to monitor the integrity of the adhesion layer, for reasons stated above in the capacitance embodiment.

Figure 6A:
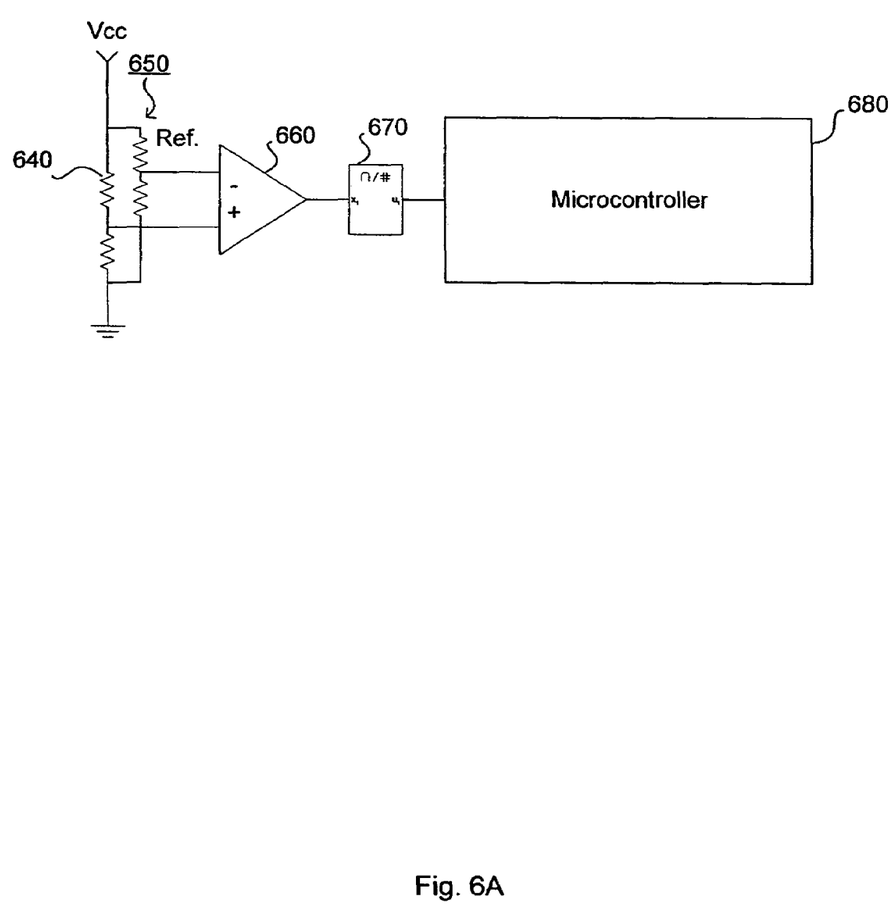
FIG. 6A is a circuit diagram of an exemplary circuit that measures the temperature of an integrated thermistor.

FIG. 6A is a circuit diagram of an exemplary circuit that measures the temperature of a percutaneous electrode array comprising an integrated thermistor. In this embodiment, thermistor element 640 is connected to a monitoring circuit comprising a voltage divider bridge circuit 650, a differential amplifier 660, an analog-to-digital converter 670 and a microcontroller 680. Amplifier 660 eliminates any common mode noise associated with the lead length from the element 640 to the monitoring circuit. The resultant voltage from amplifier 660 varies as a function of array temperature The monitoring circuit converts the voltage signal to a binary value by analog-to-digital converter 670. The monitoring circuit further comprises microcontroller 680 having software that converts the binary representation of the voltage signal into the temperature of the array.

Figure 6B:
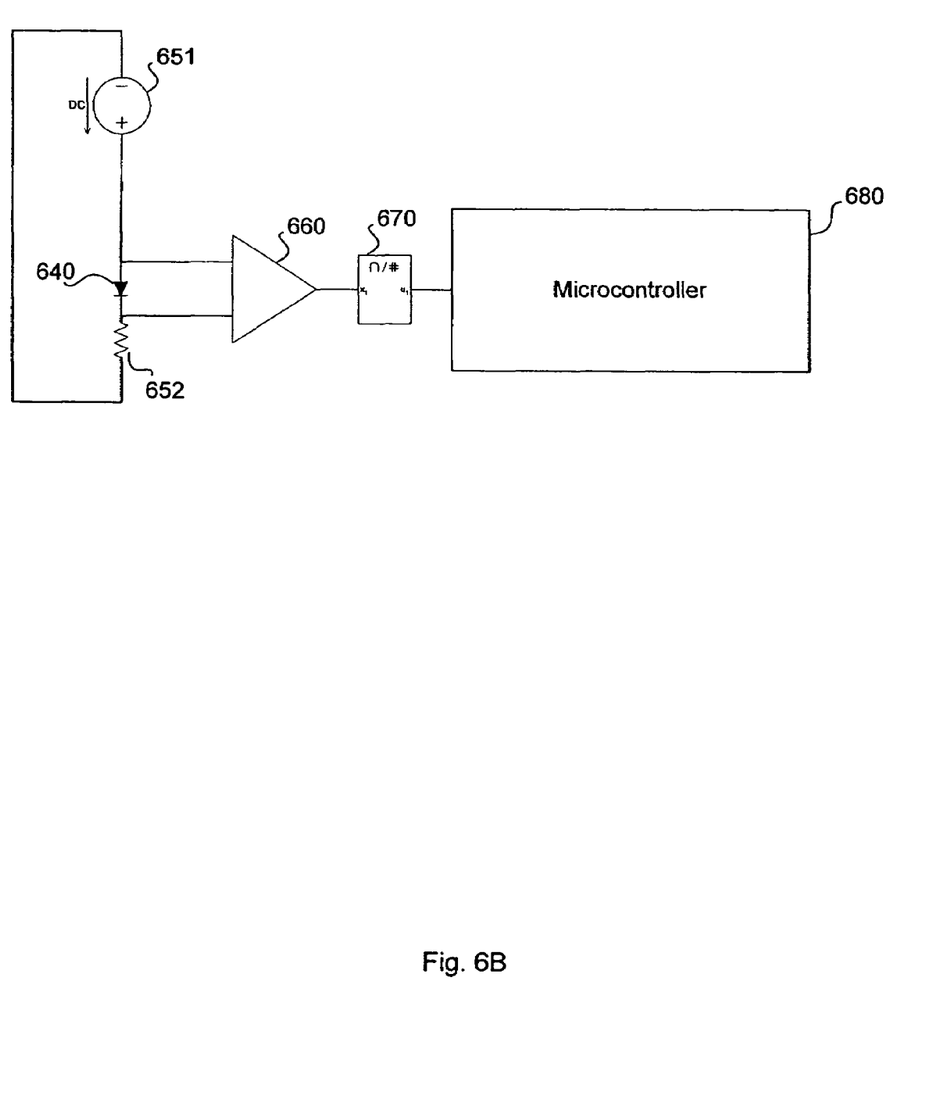
FIG. 6B is a circuit diagram of an exemplary circuit that measures the temperature of an integrated semiconductor junction.

FIG. 6B is a circuit diagram of an exemplary circuit that measures the temperature of a percutaneous electrode array comprising either an integrated semiconductor or discrete-device semiconductor junction. In this embodiment, element 640 comprises a diode or transistor having a well-characterized, temperature dependent behavior that measures temperature to a high precision. As shown in FIG. 6B, the junction is connected to a monitoring circuit comprising a constant current source 651, a reference resistor 652, an amplifier 660, an analog-to-digital converter 670, and a microcontroller 680. The current is supplied to junction 640 through resistor 652 to forward bias junction 640. A voltage is measured across junction 640, which varies with junction temperature. The relationship between the junction voltage and temperature is:

Vjunction=kT/q * ln(Ijunction/Ijunction saturation current), where k is Boltzmann's constant ($1.38 \times 10^{-23}$ J/K), T is the absolute temperature in degrees Kelvin, q is the electron charge ($1.601 \times 10^{-19}$ coulomb), Ijunction is the constant supplied reference current, and Ijunction saturation current is the saturation current of the semiconductor device ($2 \times 10^{-16}$ A for silicon).

Amplifier 660 increases the junction voltage to a useful level and converter 670 transforms the signal into a binary representation. Microcontroller 680 uses the binary representation to determine the array temperature.

Figure 6C:
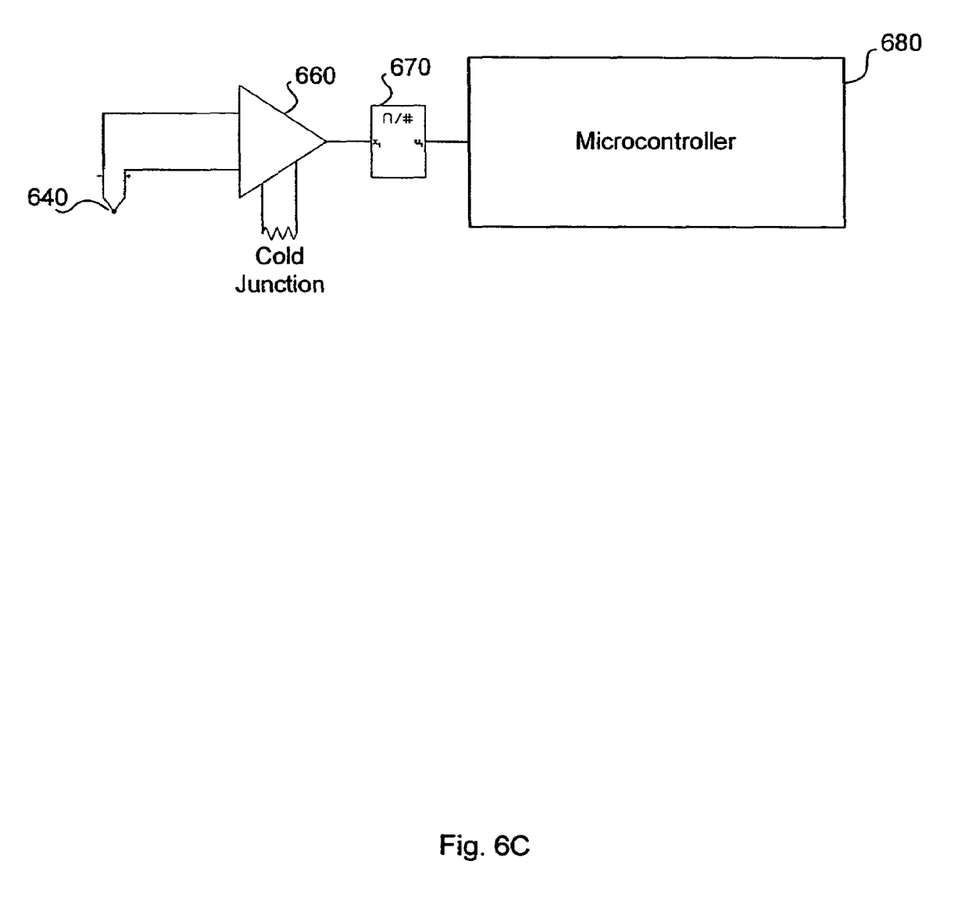
FIG. 6C is a circuit diagram of an exemplary circuit that measures the temperature of a thermocouple.

FIG. 6C is a circuit diagram of an exemplary circuit that measures the temperature of a percutaneous electrode array comprising a thermocouple. In this embodiment, temperature element 640 comprises a thermocouple. A thermocouple is a device comprising two dissimilar metals (e.g., platinum and rhodium) in electrical contact with each other at a junction. The device generates an electromotive force correlated to the temperature at the junction. The thermocouple requires compensation for the temperature of the junctions formed between the device and its connecting leads (cold-junction compensation).

The monitoring circuit illustrated in FIG. 6C comprises an amplifier 660, a analog-to-digital converter 670 and a microcontroller. Amplifier 660 amplifies thermocouple 640's output voltage, converter 670 converts it to a binary representation, and then software in microcontroller 680 uses the binary voltage value to determine the array's temperature. Amplifier 660 contains the necessary components to effect cold-junction compensation circuitry as is well known in the art. The software contains a lookup table as is well known in the art to convert the binary representation of thermocouple voltage to temperature.

In a preferred embodiment, the measured temperature parameter is used as an interlock in the electro-therapy generator device to protect the patient from harm. If for some reason the array rises above 40 degrees Celsius, or ramps up in temperature at a higher rate than would normally be expected, a temperature-monitoring portion of the electro-therapy generator device can interrupt its output, thus lessening or eliminating the possibility of a burn or thermal irritation. Such detected conditions are used to inform the operator of potential problems with the integrity of the percutaneous electrode array, or the adhesion or placement of the array, two of the most likely causes of an increase in current density.

In another embodiment, the electro-therapy generating device continuously monitors the impedance of the percutaneous electrode array. The device includes a warning indicator which alerts the operator when the impedance of the percutaneous electrode array is too high, indicating that the array should be checked or replaced. The indicator would provide one or more of a visual indication, for example a blinking light emitting diode (LED) or an error message on an liquid crystal display (LCD), an audio indication such as a beeping sound, and a sensory indication such as a vibration producing device. The warning indicator can also be used to indicate error conditions such as a loose array, unplugged lead wires, weak batteries, missing temperature signal, missing capacitance monitoring signal, or any other defective condition of the array.

While the invention has been described with reference to preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for this invention, but that the invention will include all embodiments falling within the scope of the appended claims.

What is claimed is:

1. A method of producing a percutaneous electrode array comprising:

micromachining a master mold of a perctaneous electrode array having a substrate and a plurality of electrodes from silicon using semiconductor lithographic processing;

creating a replica mold by electroplating thin film silver followed by nickel onto the master mold;
heating, softening, and rolling a polymeric film;
forcing the film into the replica mold using pressure to form an array structure; and
cooling the array structure and removing the structure from the replica mold.

2. The method of claim 1, further comprising:
thermally processing array material to form a carbonized structure; and
depositing an adhesive layer on the structure.

3. The method of claim 1, wherein the polymeric film comprises polymethyl methacrylate.

4. The method of claim 1, further comprising spraying conductive inks onto the structure and heating the structure to form a conductive coating.

5. The method of claim 1, further comprising:
spraying, dipping or spin coating an indium tin oxide precursor onto the array structure; and
heating the structure to form a conductive film coating.

6. The method of claim 1, further comprising forming a conductive film comprising indium tin oxide by evaporation or sputtering processes onto the array structure.

* * * * *